(12) United States Patent
Gorensek et al.

(10) Patent No.: US 7,201,775 B2
(45) Date of Patent: Apr. 10, 2007

(54) STABILIZING DEVICE FOR INTERVERTEBRAL DISC, AND METHODS THEREOF

(76) Inventors: Bogomir Gorensek, Hauptmanca 58, Ljubljana, Slovenia (SI); Sean Kavanaugh, P.O. Box 859, Eastham, MA (US) 02642

( * ) Notice: Subject to any disclaimer, the term of this patent is extended or adjusted under 35 U.S.C. 154(b) by 159 days.

(21) Appl. No.: 10/669,951

(22) Filed: Sep. 24, 2003

(65) Prior Publication Data
US 2004/0230305 A1 Nov. 18, 2004

Related U.S. Application Data

(60) Provisional application No. 60/413,111, filed on Sep. 24, 2002.

(51) Int. Cl.
*A61F 2/44* (2006.01)
*A61B 17/00* (2006.01)

(52) U.S. Cl. ............................ 623/17.11; 623/17.16; 606/80

(58) Field of Classification Search ............ 623/17.11, 623/17.12, 17.13, 17.14, 17.15, 17.16, 18.11; 606/80, 72, 61, 79; 30/352
See application file for complete search history.

(56) References Cited

U.S. PATENT DOCUMENTS

| | | | |
|---|---|---|---|
| 3,527,841 A * | 9/1970 | McIntire et al. ............ 528/354 |
| 3,921,632 A | 11/1975 | Bardani | |
| 4,473,070 A | 9/1984 | Matthews et al. | |
| 4,542,539 A * | 9/1985 | Rowe et al. .............. 623/23.57 |
| 4,665,906 A | 5/1987 | Jervis | |
| 4,714,469 A | 12/1987 | Kenna | |
| 4,772,287 A | 9/1988 | Ray et al. | |
| 4,782,833 A | 11/1988 | Einhorn et al. | |
| 4,871,094 A | 10/1989 | Gall et al. | |
| 4,904,260 A | 2/1990 | Ray et al. | |
| 4,911,720 A * | 3/1990 | Collier ..................... 623/23.12 |
| 4,936,848 A | 6/1990 | Bagby | |
| 4,961,740 A | 10/1990 | Ray et al. | |

(Continued)

FOREIGN PATENT DOCUMENTS

EP 0700671 3/1996

(Continued)

OTHER PUBLICATIONS

Bagga C.S., Williams P., Highma P.A., Bao B.Q. "Development of Fatigue Test Model for a Spinal Nucleus Prosthesis with Preliminary Results for a Hydrogel Spinal Prosthetic Nucleus." Proceedings of the 1997 Bioengineering Conference, 441-442: BED-vol. 35, Sunriver, Oregon, Jun. 11-15, 1997.

Bao Q.B., Bagga C.S., "The Dynamic Mechanical Analysis of Hydrogel Elastomers." Thermochimica Acta, 226:107-113 (1993).

Martz E.O., Goel V.K., Pope M.H., Park J.B. "Materials and Design of Spinal Implants—A Review." Journal of Biomedical Materials Research, vol. 38, Issue 3:267-288 (1997).

Bao Q.B., McCullen G.M., Higham P.A., Dumbleton J.H., Yuan H.A. "The Artificial Disc: Theory, Design and Materials" Biomaterials, vol. 17, No. 12:1157-1167 (1996).

(Continued)

*Primary Examiner*—Pedro Philogene
(74) *Attorney, Agent, or Firm*—Knobbe, Martens, Olson & Bear, LLP; Sean Kavanaugh

(57) ABSTRACT

An implantable device for stabilizing joints is provided. The stabilizing device, or implant, includes an elongated body and at least two bone cutting surfaces. The bone cutting surfaces are adapted to cut bone upon rotation of the body about its longitudinal axis between two bones. The device is adapted to promote bone fusion. In one embodiment, a device to initiate bony fusion between two adjacent vertebral bodies in the spine is provided. Methods of stabilizing joints and promoting bone fusion are also provided.

37 Claims, 14 Drawing Sheets

U.S. PATENT DOCUMENTS

| | | |
|---|---|---|
| 5,026,373 A | 6/1991 | Ray et al. |
| 5,047,055 A | 9/1991 | Bao et al. |
| 5,055,104 A | 10/1991 | Ray |
| 5,061,274 A | 10/1991 | Kensey |
| 5,100,422 A | 3/1992 | Berguer et al. |
| 5,108,420 A | 4/1992 | Marks |
| 5,116,357 A | 5/1992 | Eberbach |
| 5,171,280 A | 12/1992 | Baumgartner |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,207,649 A | 5/1993 | Aruny |
| 5,219,359 A | 6/1993 | McQuilkin et al. |
| 5,239,982 A | 8/1993 | Trauthen |
| 5,292,332 A | 3/1994 | Lee |
| 5,342,394 A | 8/1994 | Matsuno et al. |
| 5,356,432 A | 10/1994 | Rutkow et al. |
| 5,445,639 A * | 8/1995 | Kuslich et al. ............ 606/80 |
| 5,489,308 A | 2/1996 | Kuslich et al. |
| 5,514,130 A | 5/1996 | Baker |
| 5,522,898 A | 6/1996 | Bao |
| 5,534,028 A | 7/1996 | Bao et al. |
| 5,556,429 A | 9/1996 | Felt |
| 5,562,736 A | 10/1996 | Ray et al. |
| 5,591,204 A | 1/1997 | Janzen et al. |
| 5,634,936 A | 6/1997 | Linden et al. |
| 5,645,597 A | 7/1997 | Krapiva |
| 5,674,295 A | 10/1997 | Ray et al. |
| 5,690,674 A | 11/1997 | Diaz |
| 5,702,454 A | 12/1997 | Baumgartner |
| 5,705,780 A | 1/1998 | Bao |
| 5,716,408 A | 2/1998 | Eldridge et al. |
| 5,716,416 A | 2/1998 | Lin |
| 5,743,917 A | 4/1998 | Saxon |
| 5,746,765 A | 5/1998 | Kleshinski et al. |
| 5,755,797 A | 5/1998 | Baumgartner |
| 5,785,705 A | 7/1998 | Baker |
| 5,800,549 A | 9/1998 | Bao et al. |
| 5,824,093 A | 10/1998 | Ray et al. |
| 5,846,261 A | 12/1998 | Kotula et al. |
| 5,888,220 A | 3/1999 | Felt et al. |
| 5,919,235 A | 7/1999 | Husson et al. |
| 5,976,174 A | 11/1999 | Ruiz |
| 5,976,186 A | 11/1999 | Bao et al. |
| 5,980,504 A | 11/1999 | Sharkey et al. |
| 6,019,793 A | 2/2000 | Perren et al. |
| 6,024,096 A | 2/2000 | Buckberg |
| 6,102,930 A | 8/2000 | Simmons, Jr. |
| 6,113,639 A | 9/2000 | Ray et al. |
| 6,120,539 A | 9/2000 | Eldridge et al. |
| 6,126,682 A | 10/2000 | Sharkey et al. |
| 6,132,465 A | 10/2000 | Ray et al. |
| 6,174,311 B1 * | 1/2001 | Branch et al. ............ 606/61 |
| 6,179,836 B1 | 1/2001 | Eggers et al. |
| 6,190,353 B1 | 2/2001 | Makower et al. |
| 6,224,630 B1 | 5/2001 | Bao et al. |
| 6,224,631 B1 * | 5/2001 | Kohrs ............ 623/17.11 |
| 6,231,597 B1 | 5/2001 | Deem et al. |
| 6,245,107 B1 | 6/2001 | Ferree |
| 6,264,695 B1 | 7/2001 | Stoy |
| 6,280,475 B1 | 8/2001 | Bao et al. |
| 6,287,343 B1 | 9/2001 | Kuslich et al. |
| 6,371,990 B1 | 4/2002 | Ferree |
| 6,402,750 B1 | 6/2002 | Atkinson et al. |
| 6,419,704 B1 | 7/2002 | Ferree |
| 6,428,575 B2 | 8/2002 | Koo et al. |
| 6,428,576 B1 | 8/2002 | Haldimann |
| 6,491,690 B1 | 12/2002 | Goble et al. |
| 6,520,967 B1 | 2/2003 | Cauthen |
| 6,537,320 B1 | 3/2003 | Michelson |
| 6,579,291 B1 | 6/2003 | Keith et al. |
| 6,592,625 B2 | 7/2003 | Cauthen |
| 6,635,087 B2 | 10/2003 | Angelucci et al. |
| 6,712,853 B2 | 3/2004 | Kuslich |
| 6,719,797 B1 | 4/2004 | Ferree |
| 6,726,696 B1 | 4/2004 | Houser et al. |
| 6,783,546 B2 | 8/2004 | Zucherman et al. |
| 6,805,695 B2 | 10/2004 | Keith et al. |
| 6,821,276 B2 | 11/2004 | Lambrecht et al. |
| 6,855,166 B2 * | 2/2005 | Kohrs ............ 623/17.11 |
| 2001/0004710 A1 | 6/2001 | Felt et al. |
| 2002/0049498 A1 | 4/2002 | Yuksel et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147496 A1 | 10/2002 | Belef et al. |
| 2002/0151980 A1 | 10/2002 | Cauthen |
| 2002/0165542 A1 | 11/2002 | Ferree |
| 2002/0183846 A1 | 12/2002 | Kuslich et al. |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0040796 A1 | 2/2003 | Ferree |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2003/0149438 A1 | 8/2003 | Nichols et al. |
| 2004/0002764 A1 | 1/2004 | Gainor et al. |
| 2004/0133229 A1 | 7/2004 | Lambrecht et al. |
| 2004/0138673 A1 | 7/2004 | Lambrecht et al. |
| 2005/0004578 A1 | 1/2005 | Lambrecht et al. |

FOREIGN PATENT DOCUMENTS

| | | |
|---|---|---|
| EP | 1091776 | 5/2004 |
| EP | 1214026 | 4/2005 |
| EP | 1180978 | 5/2005 |
| FR | 2639823 A1 | 6/1990 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | WO 95/26689 | 10/1995 |
| WO | WO 95/31946 | 11/1995 |
| WO | WO 95/34331 | 12/1995 |
| WO | WO 97/26847 | 7/1997 |
| WO | WO 98/17190 | 4/1998 |
| WO | WO 98/20939 | 5/1998 |
| WO | WO 98/38918 | 9/1998 |
| WO | WO 99/02108 | 1/1999 |
| WO | WO 00/44288 | 8/2000 |
| WO | WO 00/62832 | 10/2000 |
| WO | WO 01/10316 | 2/2001 |
| WO | WO 01/21246 | 3/2001 |
| WO | WO 01/28464 | 4/2001 |
| WO | WO 01/28468 | 4/2001 |
| WO | WO 01/45577 | 6/2002 |
| WO | WO 02/058599 | 8/2002 |
| WO | WO 02/067824 | 9/2002 |

OTHER PUBLICATIONS

Sakalkale D.P., Bhagia S.A., Slipman C.W. "A Historical Review and Current Perspective on the Intervertebral Disc Prosthesis." Pain Physician, vol. 6, No. 2:1-4 (2003).

Lemaire J.P., Skalli W., Lavaste F., Templier A., Mendes, F., Diop A., Sauty V., Laloux E. "Intervertebral Disc Prosthesis." Clinical Orthopaedics and Related Research, No. 337:64-76 (1997).

Langrana N.A., Parsons J.R., Lee C.K., Vuono-Hawkins M., Yang S.W., Alexander H. "Materials and Design Concepts for an Intervertebral Disc Spacer. I. Fiber-Reinforced Composite Design" Journal of Applied Biomaterials, vol. 4:125-132 (1994).

Bao Q.B., Yuan H.A. "Artificial Disc Technology".Neurosurg Focus 9(4), 2000.

Hedman T.P., Kostuik J.P., Femie G.R., Hellier W.G. "Design of an Intervertebral Disc Prosthesis" Spine 16 (Suppl. 6):S256-S260 (1991).

Husson J.L., Scharer N., Le Nihouannen J.C., Freudiger S., Baumgartner W., Polard J.L. "Nucleoplasty During Discectomy Concept and Experimental Study." Rachis vol. 9, No. 3:145-152 (1997).

Husson J.L., Baumgartner W., Le Huec J.C. "Nucléoplastie Inter-Somatique Par Voie Postérieure Per-Dissectomie: Concept et Étude Expérimentale." Restabillisation Inter-Somatique Due Rachis Lombaire: 311-320 (1996).

Ray C.D., Schonmayr R., Kavanagh S.A., Assell R. "Prosthetic Disc Nucleus Implants." Riv. Neuroradiol 1999:12 (Suppl. 1):157-162.

Schonmayr R., Busch C., Lotz C., Lotz-Metz G. "Prosthetic Disc Nucleus Implants: The Wiesbaden Feasibility Study, 2 Years follow-up in Ten patients" Riv. Neuroradiol 1999:12 (Suppl. 1):163-170.

Zelentsov E.V. "Plastic Surgery with Collagen of Intervertebral Discs for Surgical Treatment of Lumbosacral Polyradiculitis." Abstract of a thesis, Leningrad, 1990.

USSR Author's Certificate No. 1477390 "Method for Treatment of Osteochondritis." Published May 17, 1989.

USSR Author's Certificate No. 1827204 "Method for Treatment of Spinal Osteochondritis." Published May 15, 1993.

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Sheljakin S. Ju. "Percutaneous Diskectomy Skin-through Discectomy in Complex Treatment of Patients with Disc Lumbosacral Polyraduculitis." Abstract of a thesis, St. Petersburg, 1996.

Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.

Shul'man Kh.M. "Surgical Treatment of Compression Type Osteochondritis of Spinal Lumbar Region with Intervertebral Disc Implantation." Kazan'. 1980, pp. 174-185.

Shul'man Kh.M. Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosugery. Kazan', 1976, pp. 22-27.

Usmanov M.M. "Intervertebral Disc Changes at Local Damage of its Elements and Implantation of Various Materials." Abstract of a thesis Moscow, 1991.

Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

* cited by examiner

STABILIZING DEVICE FOR INTERVERTEBRAL DISC, AND METHODS THEREOF

CROSS REFERENCE TO RELATED APPLICATIONS

This application claims the benefit of U.S. Provisional Patent Application Ser. No. 60/413,111, which was filed on Sep. 24, 2002 and which is incorporated herein by reference.

BACKGROUND OF THE INVENTION

1. Field of the Invention

This invention pertains to surgical stabilizing devices and procedures for stabilizing joints within the spine, and other joints. More particularly, this invention pertains to a novel stabilizing device that utilizes one or more local bone autografts harvested during the implantation procedure.

2. Description of the Related Art

The treatment of back pain can be relieved by preventing relative motion between spinal vertebrae. Intervertebral stabilization achieved by the use of spine cages, intervertebral spacers, and bone grafts for insertion into the space formerly occupied by a degenerated disc are known in the art. These devices may involve mechanically coupling the adjacent vertebrae or by promoting fusion between them. Accordingly, such techniques are used to stabilize the spine and reduce pain by rigidly joining two adjacent vertebrae that oppose a degenerated disc or degenerated posterior elements of the vertebrae (e.g. facet joints).

SUMMARY OF THE INVENTION

In one embodiment of the current invention, an implantable stabilizing device for stabilizing two adjacent vertebral bodies in the human spine is provided. The stabilizing device, or implant, comprises an elongated body, having a longitudinal axis and a transverse axis, and at least two bone cutting surfaces. In one embodiment, the elongated body has a first bone cutting surface and a second bone cutting surface that are offset from the longitudinal axis of the body. The first bone cutting surface faces in a first direction, and the second bone cutting surface faces in a second direction. The first bone cutting surface and/or the second bone cutting surface is adapted to cut bone upon rotation of the body about its longitudinal axis between two adjacent vertebral bodies.

In several embodiments, the bone cutting surfaces are blades or blade-like surfaces. In one embodiment, the first bone cutting surface, the second bone cutting surface and/or the elongated body has one or more perforations, holes, or voids. In another embodiment, the first bone cutting surface, the second bone cutting surface and/or the elongated body is made of a material that is at least partially porous.

In one embodiment, at least a portion of the elongated body is hollow. In some embodiments, the elongated body is a support member that serves to connect two bone cutting blades.

In one embodiment, at least one bone cutting surface comprises one or more teeth. In another embodiment, at least one bone cutting surface is curved inward relative to the elongated body. In one embodiment, at least one bone cutting surface is sharpened. In another embodiment, at least one bone cutting surface is blunt.

In several embodiments, a portion of a bone cutting surface and/or the elongated body includes at least one shearing means or protrusions. Protrusions include, but are not limited to, barbs, spikes and wedges. In some embodiments, a portion of a bone cutting surface and/or the elongated body is treated with a surface treatment. The surface treatment includes, but is not limited to, bone growth facilitator (e.g., bone morphogenic protein) and/or adhesives (e.g., cyanoacrylate). In one embodiment, the implantable stabilizing device further includes a source or supply of bone growth facilitator.

In several embodiments, a portion of a bone cutting surface and/or the elongated body is constructed from a biocompatible material, including but not limited to titanium, steel, plastic, and ceramic.

In one embodiment of the present invention, an implantable device for stabilizing a joint is provided. In one embodiment, the joint is a spinal joint. In other embodiments, the joint is in the shoulder, wrist, ankle, knee, hip, or digits. In several embodiments, the implantable device, or implant, comprises a first bone cutting surface and a second bone cutting surface that are connected by a support member.

In one embodiment, the bone cutting surfaces include a first leading edge, a first trailing edge, a first top edge and a first bottom edge. The support member comprises a length that is mounted perpendicular to the first bone cutting surface and the second bone cutting surface and is spaced from said first bone cutting surface and second bone cutting surface by a distance in the range of about 1 cm to about 5 cm. At least one of the bone cutting surfaces is adapted to accept a local bone autograft.

In one embodiment, at least one of bone cutting surface is a blade. In another embodiment, at least one of bone cutting surface is a blade is curved inward relative to the support member.

In some embodiments, at least one edge of at least one bone cutting surface is sharpened. In some embodiments, at least one edge of at least one bone cutting surface is blunt. In one embodiment, the leading edges of both bone cutting surfaces is sharp.

In one embodiment, an implantable stabilizing device for stabilizing two adjacent vertebral bodies in the human spine is provided. In one embodiment, the stabilizing device, or implant, comprises an elongated body having a longitudinal axis and a transverse axis, a first shearing means on the elongated body offset from the longitudinal axis and a second shearing means on the elongated body offset from the longitudinal axis. The first shearing means faces in a first direction, and the second shearing means faces in a second direction. At least one of the shearing means is adapted to shear bone upon rotation of the body about its longitudinal axis between two adjacent vertebral bodies.

In one embodiment of the present invention, a method of initiating bony fusion between a first bone and a second bone is provided. In one embodiment, an implant having a body with a longitudinal axis, and at least a first bone cutter and a second bone cutter offset in opposite transverse directions from the longitudinal axis is provided. The implant is introduced between the first and second bones and rotated about its longitudinal axis so that the first and second bone cutters cut fragments from the first and second bones. The implant is left in position between the first and second bones. In one embodiment, a bone growth facilitator is infused through at least a portion of the implant. In some embodiments, a second implant is inserted in between the first and second bones.

In one embodiment, bony fusion is initiated between adjacent vertebral bodies. In one embodiment, at least one of the first and second vertebral bodies is in the sacral spine, lumbar spine or cervical spine.

In one embodiment, the implant is rotated through no more than one revolution. In another embodiment, the implant is rotated through no more than about 120 degrees. In another embodiment, rotation is stopped at a point where the first bone cutter is in contact with the first bone and the second bone cutter is in contact with the second bone.

In one embodiment of the current invention, a method of stabilizing two adjacent vertebral bodies is provided. In one embodiment, a stabilizing device having a first bone cutting surface and a second bone cutting surface connected by a support member is provided. The bone cutting surfaces comprise a leading edge, a trailing edge, a top horizontal edge and a bottom horizontal edge. The stabilizing device is oriented such that the bone cutting surface are perpendicular to the endplates of said vertebral bodies and the support member is parallel to said endplates. The stabilizing device is inserted into and across the endplates such that at least a portion of at least one of the endplates is lodged between the bone cutting surface. The stabilizing device is rotated such that at least one of the endplates is translocated perpendicular to its original location.

In one embodiment of the invention, a method of promoting bony fusion between a first bone and a second bone is provided. One or more implants having a body with a longitudinal axis, and at least a first shearing means and a second shearing means offset in opposite transverse directions from the longitudinal axis is provided. The implants are introduced in between the first and second bones. At least one of the implants is rotated about its longitudinal axis so that the first and second shearing means shear one or more fragments from the first and second bones. At least one or more implants in left in position between the first and second bones.

DETAILED DESCRIPTION OF THE PREFERRED EMBODIMENT

Several embodiments of present invention involve stabilizing devices and methods that immobilize adjacent vertebral bodies or other selected joints. One or more of the embodiments, a stabilizing device, or implant, is provided to re-establish and maintain proper alignment and distance between the adjacent vertebrae and to serve as a spacer or fusion cage. The shape of the stabilizing device offers sufficient surface area to offer initial resistance to axial compression between the adjacent end plates and over time, as fusion progresses, even greater resistance. Several embodiments of the present invention are particularly advantageous because they offer pain relief. In one embodiment, pain caused by spinal stenosis or by degenerated or herniated disc tissue is ameliorated or eliminated via discectomy and reestablishment of proper vertebral spacing. In another embodiment, pain caused by degenerated facet joints and pathological increased range of motion is reduced.

In one embodiment, the methods of autograft bone harvest and implantation are combined. Here large hunks or plates (as compared to small chips) are cleaved from a proximal bony surface as the stabilizing device is inserted between the vertebral bodies. Large chunks of bone with sufficient surface area and structural integrity are harvested. The site in which one or more of the grafts are harvested are also "prepared" in that the bone surface is scraped, or otherwise manipulated, to stimulate a healing response and promote fusion. By selecting local bone (and not bone from, for example the hip which requires addition incisions and site preparation and closing) and combing the harvesting step with the implantation step, several embodiments of the invention provide several benefits. These benefits include, but are not limited to, decreased operation time, increased surgical efficiency, patient acceptance of the stabilizing device, and effectiveness of the fusion. Although, in a preferred embodiment large portions of local bone are cleaved, one of skill in the art will understand that smaller bone fragments and/or non-local bone from other sites can be used in accordance with several embodiments of the present invention.

Figure 1:
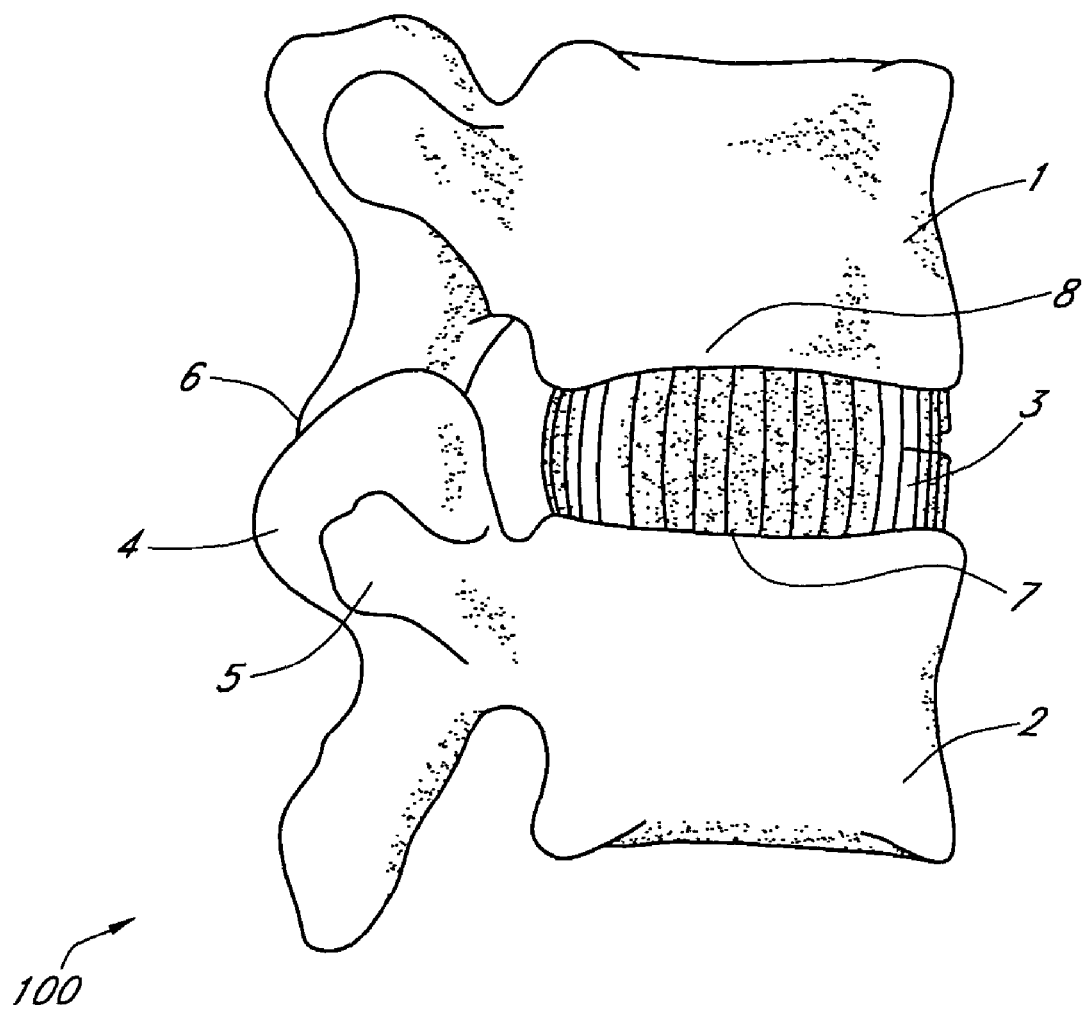
FIG. 1 shows a sagittal view of functional spinal unit.

Reference is now directed at FIG. 1, which is a sagittal view of a functional spinal unit 100 comprising a superior vertebral body 1, an anulus fibrosus 3 connected to an adjacent inferior vertebral body 2. Posterior elements of the vertebral bodies include a spinous process 4, transverse process 4 and facet joint 6. Each vertebral body has an inferior 7 and superior endplate 8 which along with the anulus fibrosus 3 bounds the nucleus pulposus.

Figure 2:
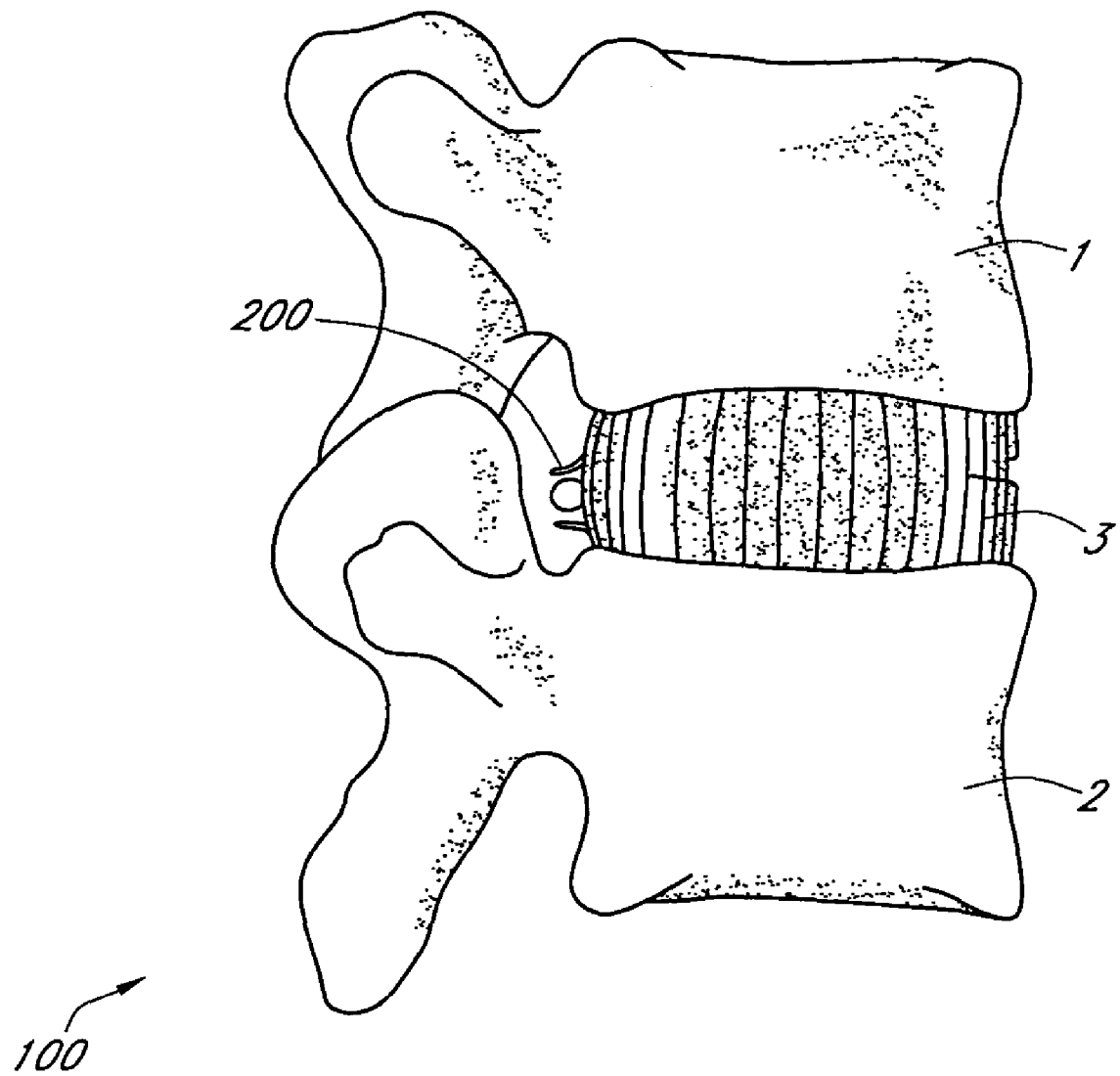
FIG. 2 shows a sagittal view of functional spinal unit with a herniated disc.

FIG. 2 shows the functional spinal unit of FIG. 1, with a herniated disc 200. Here the collagenous fibers of the anulus fibrosus 3 have broken and nucleus pulposus and anulus fibers have entered the space normally occupied by the nerves of the spinal canal.

Figure 3:
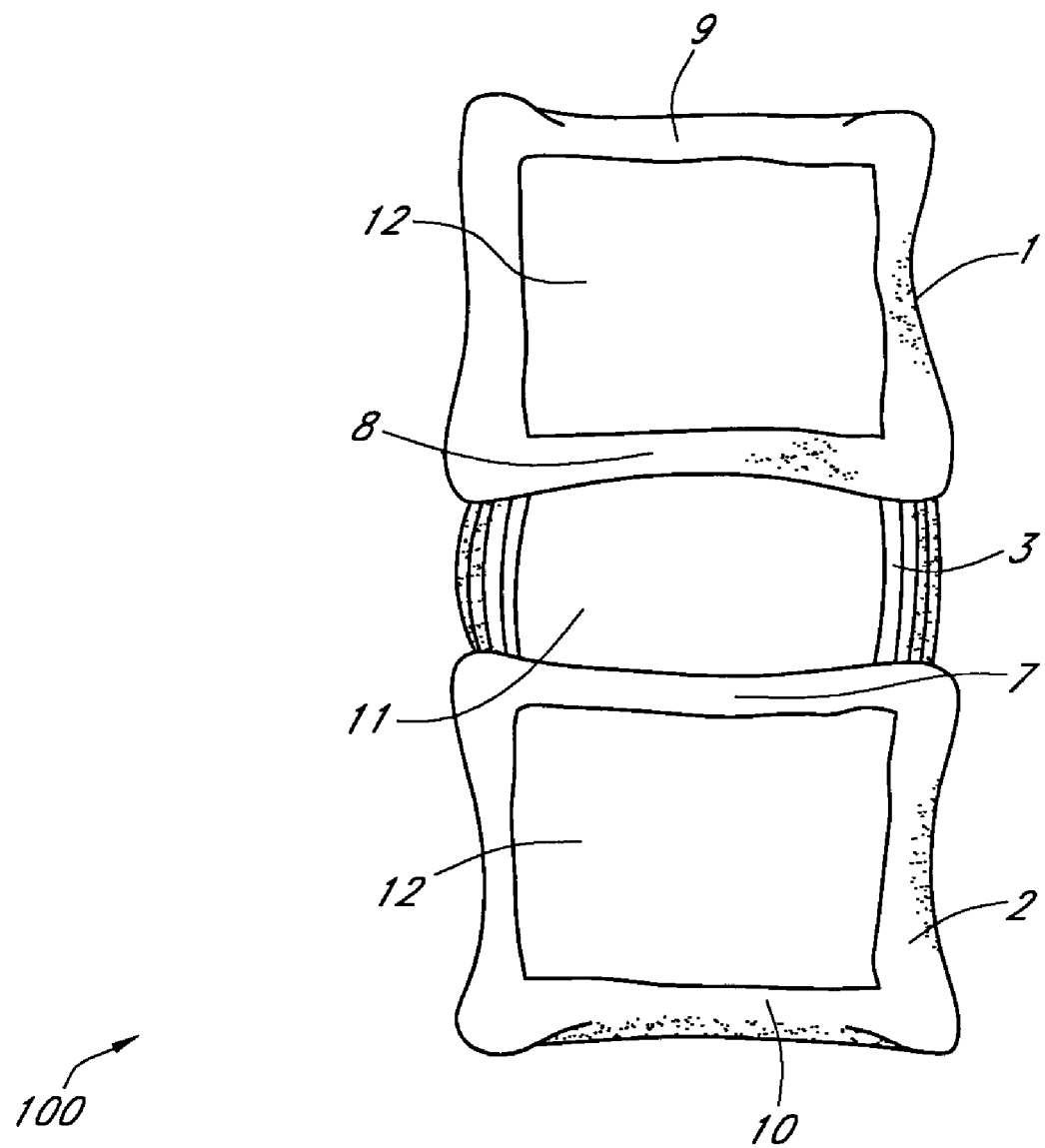
FIG. 3 shows a front cross-sectional view of a functional spinal unit.

FIG. 3 shows a front cross-sectional view of a functional spinal unit 100. The endplates 7, 8, 9, 10 are comprised of dense cortical bone near the periphery of the endplates and more porous and flexible cancellous bone towards the center. Within each vertebral body 1, 2 is marrow 12. The anulus 3 and nucleus pulposus 111 are also shown.

Figure 4A:
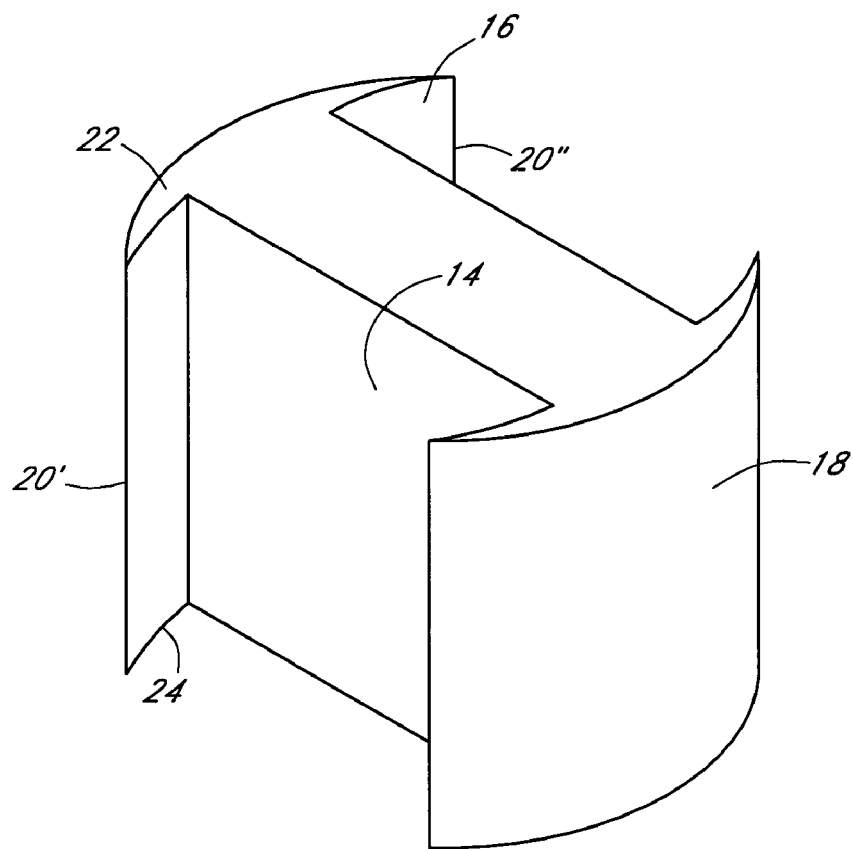
FIG. 4A, which presents an isometric view of an embodiment of the invention, FIGS. 4B and C show front view of different cross-sections of an embodiment of the invention.

FIG. 4A represents an isometric view of one embodiment of the invention. FIG. 4A shows a stabilizing device, or implant, comprising an elongated body 14 and first 16 and second 18 opposing bone cutting surfaces separated by the width of the elongated body 14. Alternatively the bone cutting surfaces could simply be connected by one or more struts or support members instead of the elongated body. Each bone cutting surface can have four sharpened edges or portions sharpened thereof such on or more of the leading, trailing, and horizontal edges of the bone cutting surfaces. In several embodiments, the first bone cutting surfaces 14 and/or the second bone cutting surfaces 16 is comprised of a plurality of bone cutting surfaces. In one embodiment, the first bone cutting surface 14 and second bone cutting surface 16 are each configured of two separate bone cutting surfaces, e.g., an upper bone cutting surface and a lower bone cutting surface. In one embodiment, the bone cutting surfaces are blades or blade-like surfaces. As shown in FIG. 4A, the elongated body 14 has a first bone cutting surface 16 and a second bone cutting surface 18 that are offset from the longitudinal axis of the body 14. The first bone cutting surface 16 faces in a first direction, and the second bone cutting surface 18 faces in a second direction. The first bone cutting surface 16 and/or the second bone cutting surface 18 is adapted to cut bone upon rotation of the body 14 about its longitudinal axis between two adjacent bones.

Figure 4B:
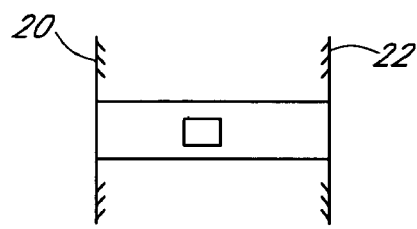
Figure 4C:
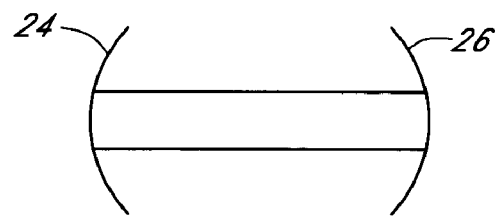

FIG. 4B and FIG. 4C show front views of different cross-sections of one embodiment of the device. FIG. 4B shows an "H"-like cross-section with straight bone cutting surfaces 20, 22, comprising bards or roughened surface to fix bone grafts. FIG. 4C shows curved bone cutting surfaces 24, 26 to trap and/or fix bone graft material. In one embodiment, a "T"-like cross-section is provided.

Figure 5:
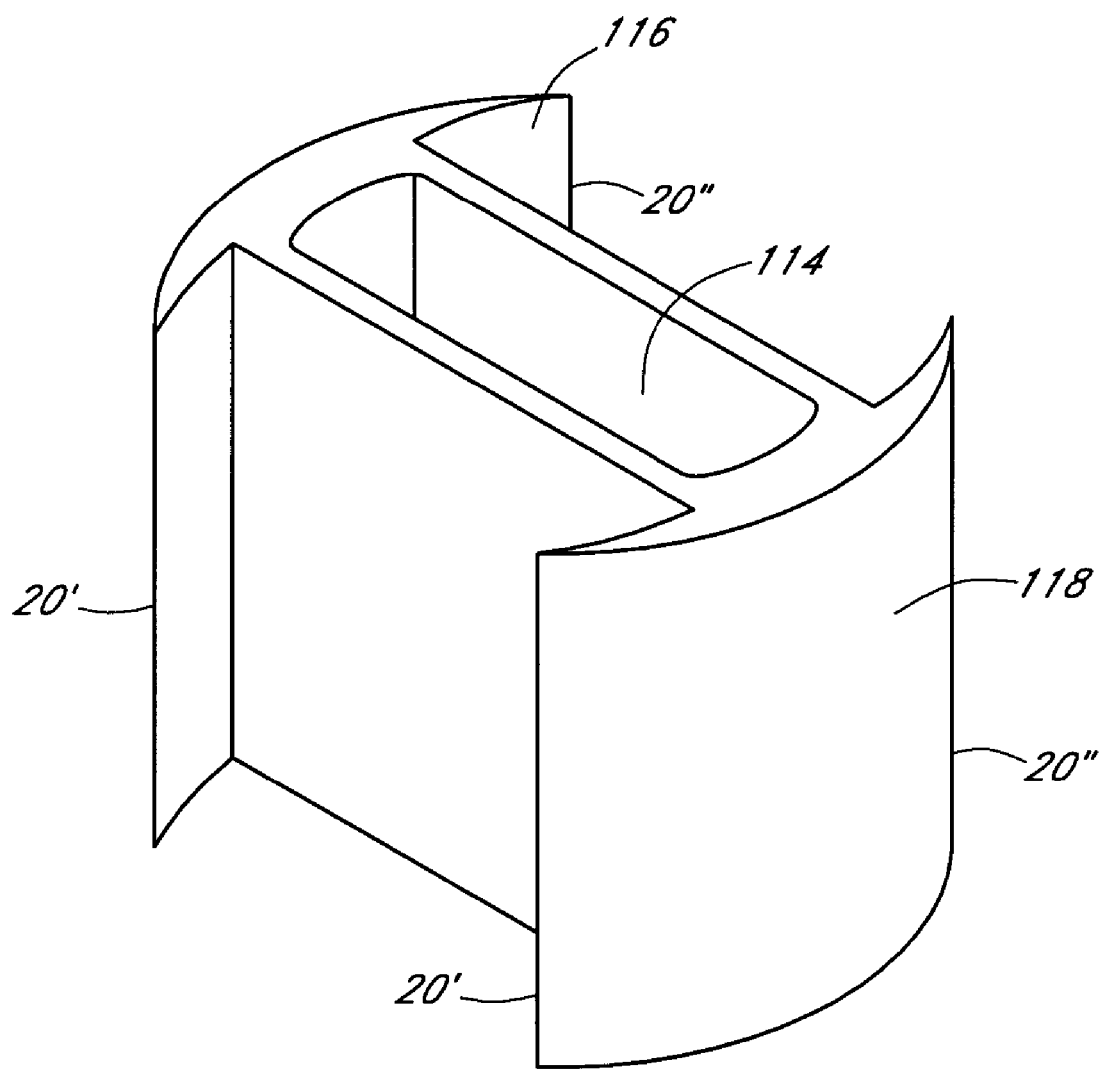
FIG. 5 is an isometric view of an alternative embodiment of the invention.

FIG. 5 is an isometric view of one embodiment of the invention showing an elongated body with a first bone cutting surface 116 and second bone cutting surface 118. The body 114 is at least partially hollow. In one embodiment, the hollowed portion is adapted to accept graft material or other biocompatible material. In one embodiment, the hollow body facilitates rotation of the stabilizing device. In embodiments where the body is not hollow, a hex-shaped insert may be cut-out of the body to facilitate rotation with compatible rods and tools. In some embodiments, the elongated body is a support member that serves to connect two bone cutting surfaces.

In one embodiment, a portion of a bone cutting surface and/or the elongated body includes at least one shearing means or protrusion. Protrusions include, but are not limited to, barbs, spikes and wedges. In some embodiments, a portion of a bone cutting surface and/or the elongated body is treated with a surface treatment, such as bone growth facilitator (e.g., bone morphogenic protein) and/or adhesives (e.g., cyanoacrylate). In one embodiment, the implantable stabilizing device further includes a source or supply of bone growth facilitator. Bone growth facilitator aids in the promotion of bone growth and/or stability and, in some embodiments, can accelerate bone fusion and decrease patient recovery times.

Figure 6:
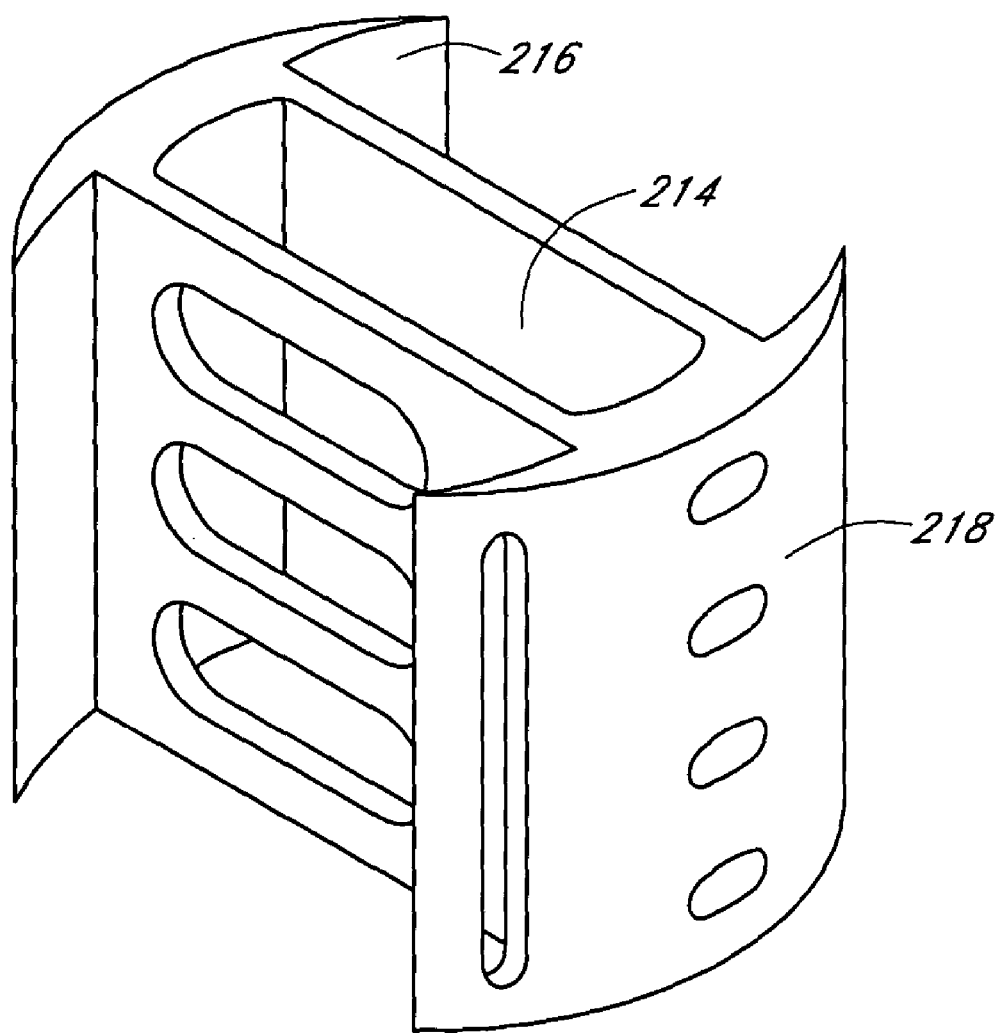
FIG. 6 is an isometric view of an alternative embodiment of the invention.

FIG. 6 shows a hollow elongated body 214, comprising one or more perforations, holes, or voids. The first bone cutting surface 216 and/or the second bone cutting surface 218 also comprises one or more perforations, holes, or voids. One function of the perforations, holes, or voids is to permit bone ingrowth and promote fusions. In one embodiment, at least one of the cutting surfaces or the body is at least partially porous. The porous material, and the perforations, holes, or voids, are also advantageous because they permit the infusion or passage of bone growth facilitator to the required sites.

Figure 7:
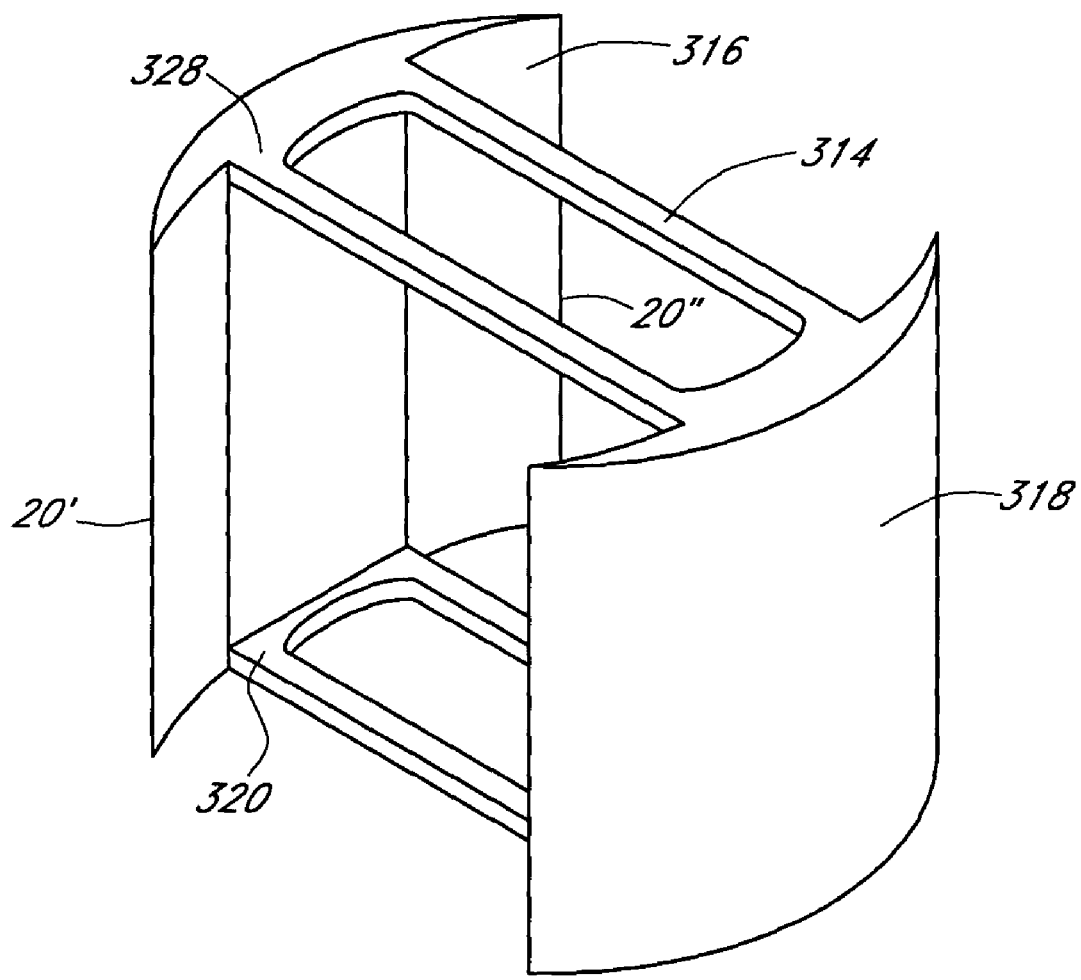
FIG. 7 is an isometric view of an alternative embodiment of the invention.

FIG. 7 expands on the concept depicted in FIG. 6 by removing substantially all of the elongated body to leave a body 314 comprising of a leading support member 328 and trailing support member 330, shown here with rectangular voids. One of skill in the art will understand that the voids can be of any shape suitable to accomplish the desired purpose, including, but not limited to, rectangular, square, triangular, oval or circular-shaped voids. In one embodiment, the first bone cutting surface 316 and/or the second bone cutting surface 318 have sharpened horizontal edges 20', 20" and can be rotated up to 360 degrees and serve to scoop, bore or core out an entire graft segment, or portions thereof. In another method, the device 500 can be rotated in the range of about 90 degrees to about 180 degrees.

Figure 8:
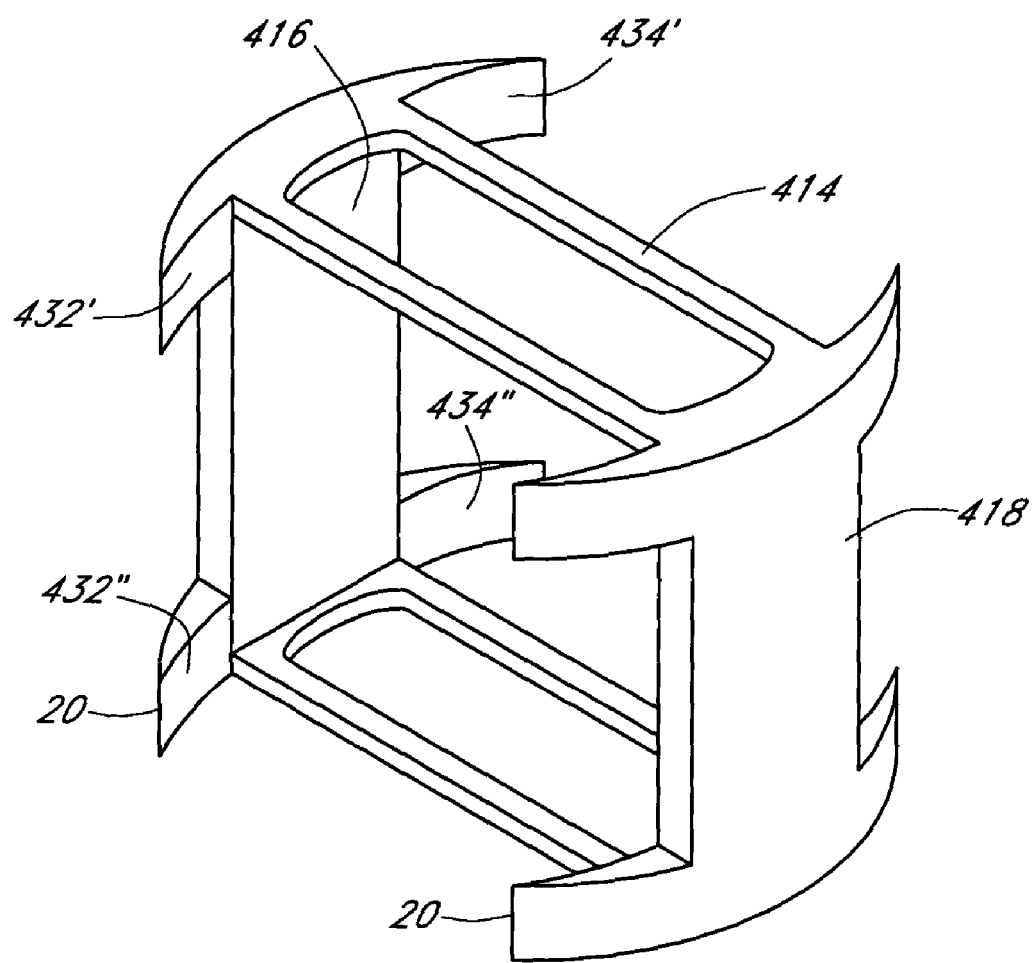
FIG. 8 is an isometric view of an alternative embodiment of the invention.

FIG. 8 shows one embodiment of the device with the first bone cutting surface 416 and second bone cutting surface 418 comprising one or more voids in the body 414 and/or bone cutting surfaces 416, 418. In one embodiment, two or more voids along the horizontal edges 20', 20" create teeth 432, 434. In one embodiment, each bone cutting surface 416, 418 has a horizontal edge 20 with leading 432', trailing upper teeth 432", and leading 434' and trailing 434" lower teeth. One skilled in the art will understand that fewer or more teeth can be used in accordance with several embodiments of the present invention.

Figure 9:
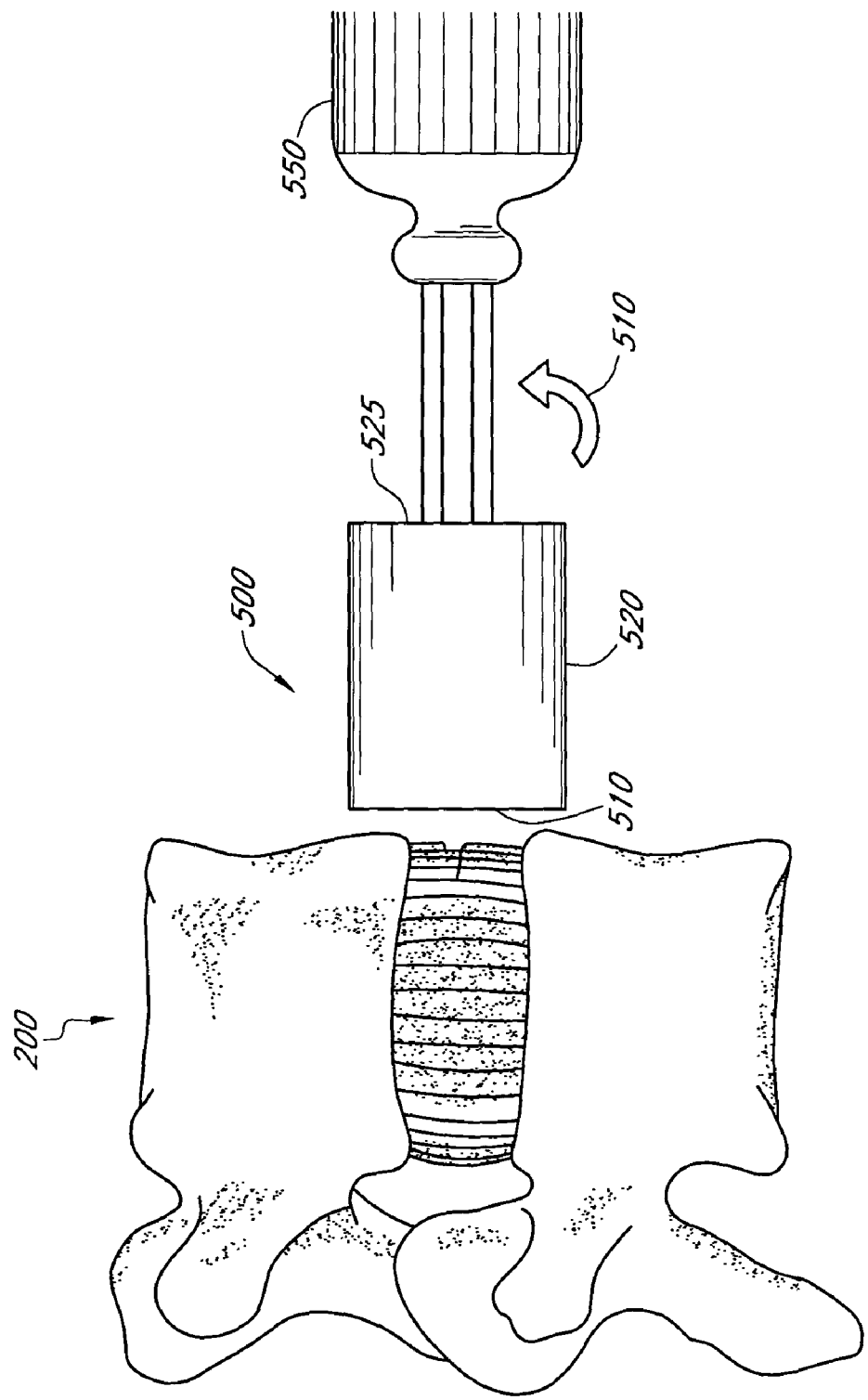
FIG. 9 is a side view of a driver device coupled to the stabilizing device.

FIG. 9 shows a side view of one embodiment of the stabilizing device 500 coupled to a driver 550. The stabilizing device, or implant, comprises a leading edge 510 and a horizontal edge 520. The coupling, engagement or connection can be a socket and sleeve, friction fit, clamp, or other connection known in the art. The driver 550 can be used as a site to apply the force of a hammer, or other like tool, to cut through the vertebrae of a herniated spine unit 200 and later as a site to apply rotational force 510 by hand or machine. According to several embodiments of the invention, the stabilizing device 500 can be a uni- or multi-component construct of biocompatible material. For example the entire stabilizing device 500, or portions thereof, could be constructed from titanium or steel, or some combination thereof. Alternatively, other metals and alloys could be employed for the bone cutting surfaces and coupled to plastic, ceramic, or other biocompatible material comprising the connection member or elongated body. Accordingly, various embodiments of the invention can be constructed from ceramics, metals, plastics, composites or any suitable biocompatible material and combinations thereof.

As discussed above, in several embodiments, various sharpened and blunt protrusions along the length and faces of the bone cutting surfaces and off of the central body of the stabilizing device can be used for shearing and cutting. For example, the sharpened protrusions on the leading edge of the bone cutting surfaces can be used to facilitate straight shearing or cutting as the stabilizing device is hammered in place prior to the rotational shearing by the blunt or sharpened horizontal edge. The shape of the bone cutting surface and its orientation with respect to the elongated body or connection members can be adapted to hold or keep harvested autograft in place by angling the bone cutting surfaces less than 90 degrees relative to the body or by curving them in ward. Barbs or surface roughness along the bone cutting surfaces and body may also be used to fix the graft to the stabilizing device.

Dimensions and Size Range

In several embodiments, the stabilizing device can be properly sized from precise dimensions of the intervertebral disc geometry of the individual selected for treatment. One skilled in the art will understand that these dimensions can be culled from CAT scan data or similar data from another modality. For example, scans can be used to determine the proper or normal distance between adjacent vertebral bodies and this distance can be used to approximate the height of the stabilizing device. Similarly, data from scans depicting the internal dimensions of the anulus and endplates (in a neutral position) can be used to design the outer shape of the device so that after harvesting bone along the endplates and rotating the stabilizing device, a precise fit is achieved. In one embodiment, the device has a width in the range of about 0.25 cm to about 7 cm, preferably between about 0.5 cm to about 6 cm, more preferably between about 1 cm to about 5 cm. In one embodiment, the device has a length in the range of about 0.25 cm to about 5 cm, preferably between about 0.5 cm to about 4 cm, more preferably between about 1 cm to about 3 cm. In one embodiment, multiple stabilizing devices are stacked between the same two vertebral bodies. Such stacking, in some embodiments, aid in stability and allow for the use of smaller stabilizing devices.

Delivery Method

In one embodiment of the present invention, a method of initiating bony fusion between a first bone and a second bone is provided. In one embodiment, an implant having a body with a longitudinal axis, and at least a first bone cutter and a second bone cutter offset in opposite transverse directions from the longitudinal axis is provided. The implant is introduced between the first and second bones and rotated about its longitudinal axis so that the first and second bone cutters cut fragments from the first and second bones. The implant is left in position between the first and second bones. In some embodiments, a second implant is inserted in between the first and second bones. In one embodiment, bony fusion is initiated between adjacent vertebral bodies. In one embodiment, at least one of the first and second vertebral bodies is in the sacral spine, lumbar spine or cervical spine. In one embodiment, the implant is rotated through no more than one revolution. In another embodiment, the implant is rotated through no more than about 120 degrees. In another embodiment, rotation is stopped at a point where the first bone cutter is in contact with the first bone and the second bone cutter is in contact with the second bone.

In one embodiment, bone growth facilitator is infused through at least a portion of the implant. Bone growth facilitator can be introduced via one or more lumens in the boring instrument or rods, described below, or can be introduced using a separate insertion device. In one embodiment, bone growth facilitator is an integral part of the stabilizing device. In some embodiments, the stabilizing device, or implant, is coupled to a source of bone growth facilitator. In alternative embodiments, the implant is pre-treated with bone growth facilitator.

In several embodiments, more than one stabilizing device is used. In one embodiment, two stabilizing devices are used. In another embodiment, three stabilizing devices are used. In one embodiment, a stabilizing device as described herein is used in connection with one or more structural devices, such as screws, that are used to stabilize the space between two bones by restricting movement.

Figure 10:
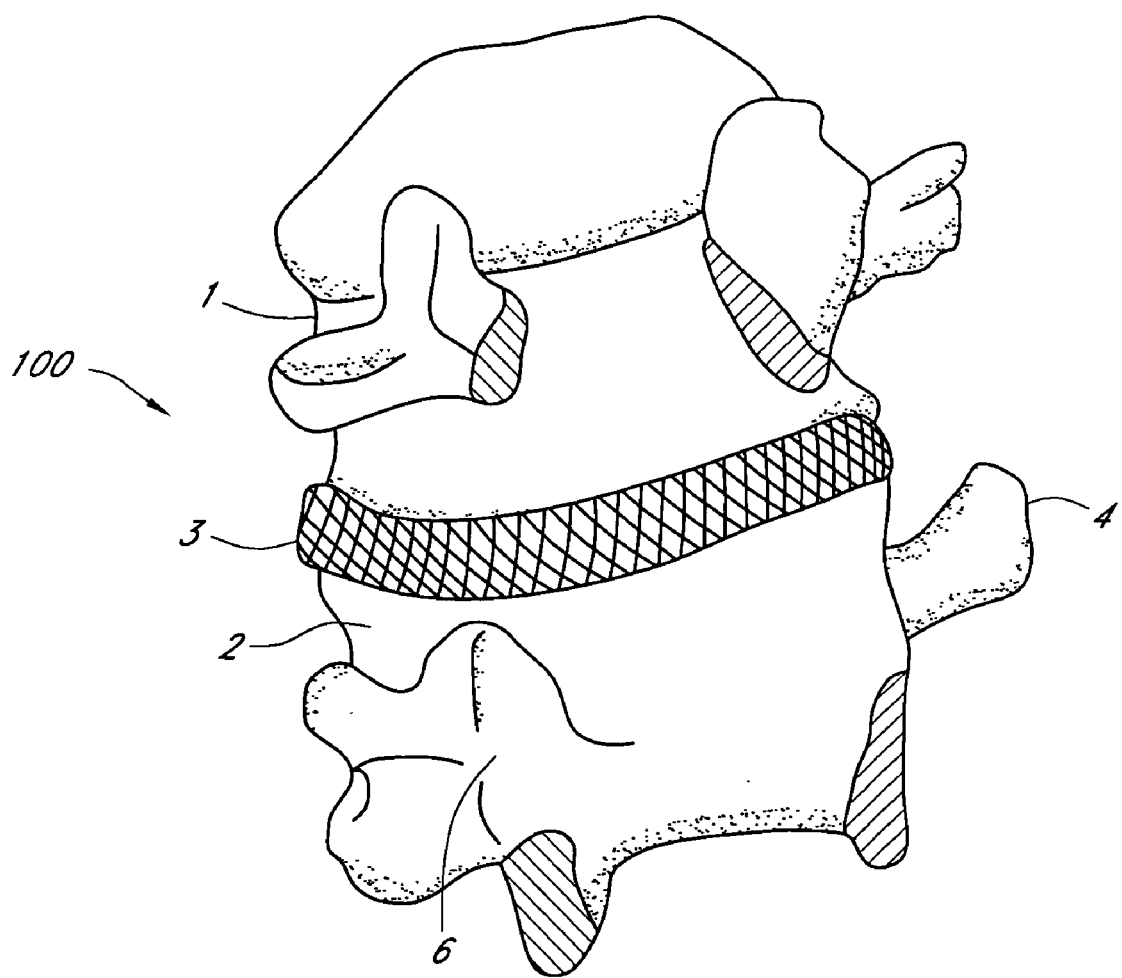
FIG. 10 is an isometric view of a functional spinal unit with the posterior elements removed.

In one embodiment, insertion of the stabilizing device is performed using an anterior approach, though a lateral approach can also be used. FIG. 10 shows an isometric view of the posterior of a functional spinal unit 100 comprising a superior vertebral body 1, inferior vertebral body 2, an anulus 3, a transverse process 4, and portion of a facet joint 6. The other posterior elements have been surgically removed. In this embodiment, a posterior approach can be used.

In one embodiment, arthroscopic equipment known in the art may be used to perform a partial or complete discectomy to provide an initial implantation site. A distraction device can then be used to provide access to the intervertebral space and allow for precise delivery. Alternatively, the stabilizing device itself can be designed with a wedge profile and forcibly inserted across the endplates thereby distracting them. An insertion rod can engage or be placed against the distal or trailing side if the device and used to push the device or as a site to apply the force of a hammer.

In an alternative delivery method, the stabilizing device can be used without performing a discectomy or distracting the endplates. In this embodiment, the leading edges of the bone cutting surfaces of the stabilizing device are also sharpened and used to cut straight into the vertebral bodies (across to the endplates) as the stabilizing device is driven between and parallel the adjacent endplates. As the stabilizing device is inserted, a hollow mid-section of the central body can accept the displaced disc material in between.

Figure 11A:
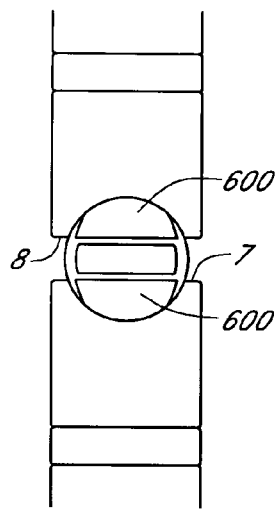
FIGS. 11A, 11B, and 11C show the rotation of a stabilizing device and translocation of local bone from the endplates of adjacent vertebral bodies.
Figure 11B:
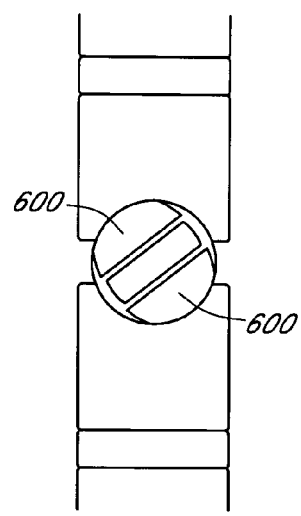
Figure 11C:
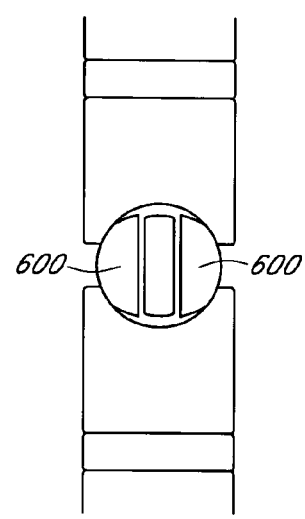

FIGS. 11A–C show a method of delivery according to one embodiment of the invention. Following the initial implantation between the vertebral bodies 7, 8, one or more drivers 550 or insertion rods are engaged to the device and used to impart axial rotation (driver is not shown) causing the bladed edges of the stabilizing device along its length to gouge and shear off portions of the adjacent endplates 7, 8. These portions are then forced into the adjacent hollow receiving zones of the stabilizing device. Barbs or other means, including, but not limited to spikes, wedges, surface treatments, adhesives (e.g., cyanoacrylate) or some combination thereof, may be used along the stabilizing device surface, or portions of the stabilizing device surface, to retain the harvested bone 600.

After rotation through approximately 90 degrees, the driver 550 or insertion rod is removed. In this orientation, the harvested bone 600 contacts the sidewalls and edges of both vertebrae that now have freshly scraped osteogenic surfaces. The curved and sharpened edges of the stabilizing device lie substantially parallel to the endplates and the harvested bone is flush with or extends beyond their edges to reduce or prevent further cutting or physical trauma. In one embodiment, a hollow stabilizing device (as shown in FIG. 7) is used to fully shear through the bone in one or more partial or complete revolutions.

Figure 12A:
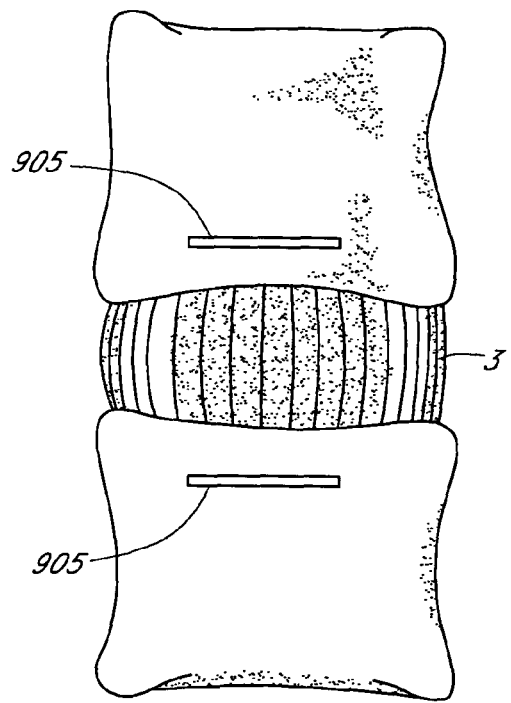
FIG. 12A shows a spinal unit with pre-delivery horizontal cuts.
Figure 12B:
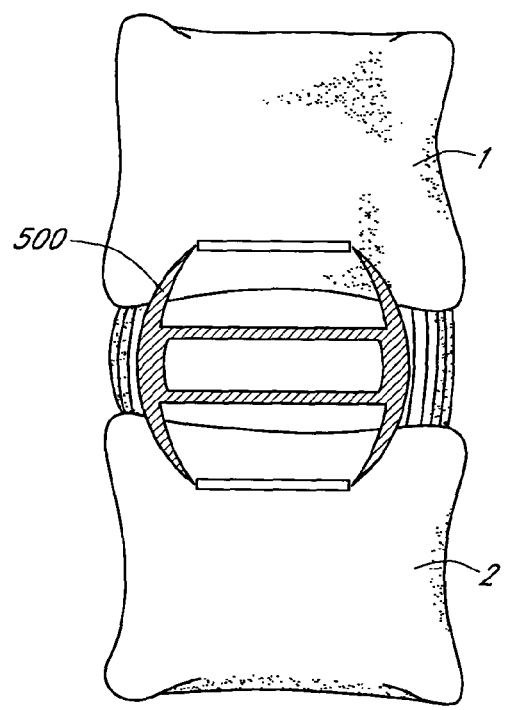
FIG. 12B shows an implanted stabilizing device prior to rotation.

FIGS. 12A and 12B show an alternative delivery method in which an initial step is added prior to inserting the stabilizing device. Here one or more horizontal holes or slots 905 are punched above each of the endplates as shown. The stabilizing device 500 is hammered into place through the endplates and across the disc space. One advantage of this step is that it facilitates rotation of the stabilizing device 500 (and displacement of the bone grafts).

Figure 13:
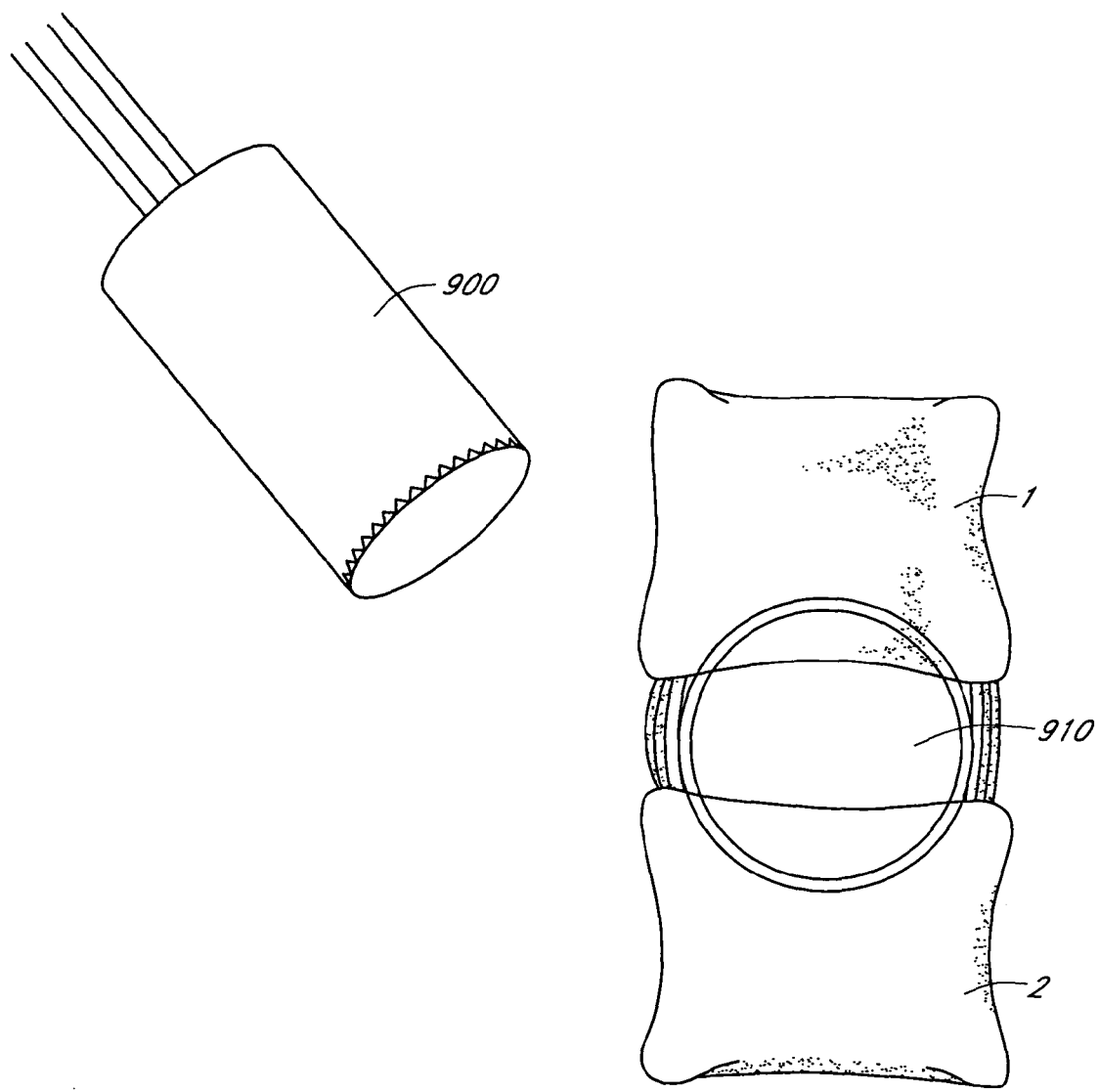
FIG. 13 shows alternative delivery method utilizing cylindrical boring device.

FIG. 13 shows a cylindrical boring instrument 900 and the cut 910 it makes into the vertebral bodies 1, 2. After the bore 900 has been removed, a device 500 with or without sharpened edges may be inserted and rotated, as described above.

In one or more embodiments discussed herein, initial fixation can be achieved through one or more of vertebral taxis (caused be the tension of the remaining anulus fibers), wedging action and friction. Secondary permanent fixation via fusion occurs over a period of weeks as the portions of the harvested bone in the stabilizing device fuse to each other and the adjacent vertebrae until eventually the stabilizing device is encapsulated.

Figure 14:
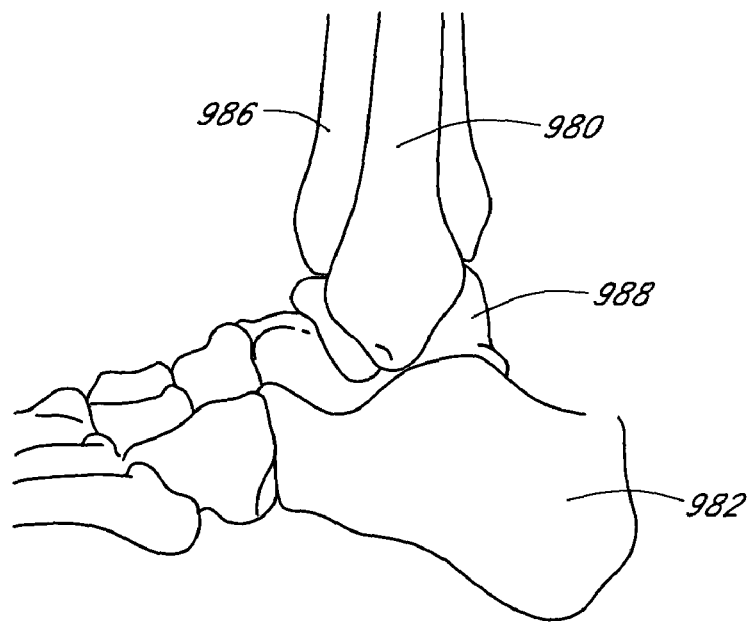
FIG. 14 is a sagittal view of an ankle joint.

In one embodiment of the invention, stabilizing devices of varying sizes and geometries are used to fuse other pathological joints of the body. These joints include, but are not limited to joints of the shoulder, wrist, ankle, knee, hip, and digits. FIG. 14 shows a sagittal view of an ankle joint, including fibula 980, tibia 986, talus 988 and calcaneus 982.

Figure 15:
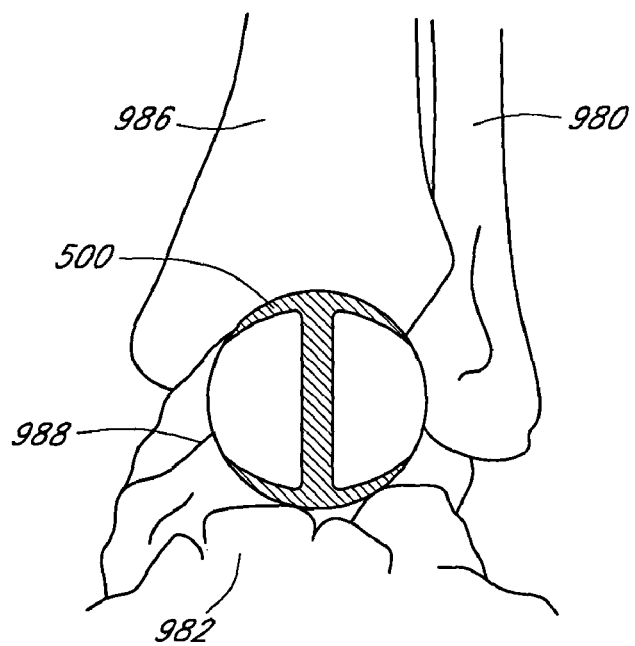
FIG. 15 is a posterior view of an ankle with an implanted stabilizing device.

FIG. 15 shows the ankle bone with an implanted stabilizing device 500. The stabilizing device 500 is used to fuse an ankle joint. In this embodiment, the stabilizing device is inserted along the bones and cartilage between the tibia 986, talus 988, calcaneus 982, an/or fibula 980. In one embodiment, the stabilizing device is implanted between two or more adjacent bones.

While this invention has been particularly shown and described with references to preferred embodiments thereof, it will be understood by those skilled in the art that various changes in form and details may be made therein without departing from the scope of the invention encompassed by the appended claims. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure.

What is claimed is:

1. An implantable stabilizing device for stabilizing two adjacent vertebral bodies in the human spine comprising:
    an elongated body having a longitudinal axis and a transverse axis;
    a first bone cutting surface on the elongated body offset from the longitudinal axis;
    a second bone cutting surface on the elongated body offset from the longitudinal axis;
    wherein the first bone cutting surface faces in a first direction, and the second bone cutting surface faces in a second direction;
    wherein said first and second bone cutting surfaces comprise a leading edge to straight cut as the implantable stabilizing device is advanced between adjacent vertebrae;
    wherein said first and second bone cutting surfaces comprise a horizontal edge to rotational cut as the implantable stabilizing device is rotated between said adjacent vertebrae; and
    wherein a width between the first bone cutting surface and the second bone cutting surface holds harvested bone during use.

2. The implantable stabilizing device of claim 1, wherein at least one of the first bone cutting surface and the second bone cutting surface is a blade.

3. The implantable stabilizing device of claim 1, wherein at least one of the first bone cutting surface and the second bone cutting surface and the elongated body comprises one or more perforations, holes, or voids.

4. The implantable stabilizing device of claim 1, wherein at least one of the first bone cutting surface, the second bone cutting surface and the elongated body is at least partially porous.

5. The implantable stabilizing device of claim 1, wherein at least a portion of the elongated body is hollow.

6. The implantable stabilizing device of claim 1, wherein at least one of the first bone cutting surface and the second bone cutting surface comprises one or more teeth.

7. The implantable stabilizing device of claim 1, wherein at least one of the first bone cutting surface and the second bone cutting surface is curved inward relative to the elongated body.

8. The implantable stabilizing device of claim 1, wherein a portion of at least one of the first bone cutting surface and the second bone cutting surface is sharpened.

9. The implantable stabilizing device of claim 1, wherein a portion of at least one of the first bone cutting surface, the second bone cutting surface and the elongated body comprises a protrusion.

10. The implantable stabilizing device of claim 9, wherein said protrusion is selected from the group consisting of: barbs, spikes and wedges.

11. The implantable stabilizing device of claim 1, wherein a portion of at least one of the first bone cutting surface, the second bone cutting surface and the elongated body comprises a shearing means.

12. The implantable stabilizing device of claim 1, wherein a portion of at least one of the first bone cutting surface, the second bone cutting surface and the elongated body comprises is treated with a surface treatment.

13. The implantable stabilizing device of claim 12, wherein said surface treatment comprises bone growth facilitator.

14. The implantable stabilizing device of claim 12, wherein said surface treatment comprises one or more adhesives.

15. The implantable stabilizing device of claim 14, wherein said adhesive is cyanoacrylate.

16. The implantable stabilizing device of claim 1, wherein a portion of at least one of the first bone cutting surface, the second bone cutting surface and the elongated body is constructed from one or more materials selected from the group consisting of: titanium, steel, plastic and ceramic.

17. The implantable stabilizing device of claim 1, further comprising a source of bone growth facilitator.

18. An implantable device for stabilizing a joint comprising:
    a first bone cutting surface and a second bone cutting surface connected by a support member;
    wherein said first bone cutting surface comprises a first leading edge to straight cut as the device is advanced between adjacent bone, a first trailing edge to rotationally cut as the implantable device is rotated between said adjacent bone; and
    wherein said second bone cutting surface comprises a second leading edge to straight cut as the device is advanced between adjacent bone, a second trailing edge to rotationally cut as the device is rotated between said adjacent bone; and,
    wherein a width between the first bone cutting surface and the second bone cutting surface holds harvested bone during use.

19. The implantable device of claim 18, wherein the support member comprises a length that is mounted perpendicular to the first bone cutting surface and the second bone cutting surface and is spaced from said first bone cutting surface and second bone cutting surface by a distance in the range of about 1 cm to about 5 cm.

20. The implantable device of claim 18, wherein at least one of the first bone cutting surface and the second bone cutting surface is adapted to accept a local bone autograft.

21. The implantable device of claim 18, wherein at least one of the first bone cutting surface and the second bone cutting surface is curved inward relative to the support member.

22. The implantable device of claim 18, wherein at least a portion of at least one of said first leading edge or said second leading edge is sharpened.

23. The implantable device of claim 18, wherein at least a portion of at least one of said first leading edge or said second leading edge is blunt.

24. The implantable device of claim 18, wherein the joint is a spinal joint.

25. The implantable device of claim 18, wherein the joint is selected from one or more joints located in the group consisting of the shoulder, wrist, ankle, knee, hip, and digits.

26. A method of initiating bony fusion between a first bone and a second bone, comprising:
   providing an implant having a body with a longitudinal axis, and at least a first bone cutter and a second bone cutter offset in opposite transverse directions from the longitudinal axis;
   introducing the implant in between the first and second bones;
   rotating the implant about its longitudinal axis so that the first and second bone cutters cut fragments from the first and second bones;
   wherein said cut fragments are harvested by the implant during use; and
   leaving the implant in position between the first and second bones.

27. A method of initiating bony fusion as in claim 26, wherein the first and second bones comprise adjacent vertebral bodies.

28. A method of initiating bony fusion as in claim 26, wherein at least one of the first and second vertebral bodies is in the sacral spine.

29. A method of initiating bony fusion as in claim 26, wherein at least one of the first and second vertebral bodies is in the lumbar spine.

30. A method of initiating bony fusion as in claim 26, wherein at least one of the first and second vertebral bodies is in the cervical spine.

31. A method of initiating bony fusion as in claim 26, wherein the rotating step comprises rotating the implant through no more than one revolution.

32. A method of initiating bony fusion as in claim 26, wherein the rotating step comprises rotating the implant through no more than about 120 degrees.

33. A method of initiating bony fusion as in claim 26, additionally comprising the step of infusing a bone growth facilitator through at least a portion of the implant.

34. A method of initiating bony fusion as in claim 26, additionally comprising the step of introducing a second implant in between the first and second bones.

35. A method of initiating bony fusion as in claim 26, comprising stopping the rotating step at a point where the first bone cutter is in contact with the first bone and the second bone cutter is in contact with the second bone.

36. A method of stabilizing two adjacent vertebral bodies comprising:
   providing a stabilizing device having a first bone cutting surface and a second bone cutting surface connected by a support member, wherein said bone cutting surfaces comprise a leading edge, a trailing edge, a top horizontal edge and a bottom horizontal edge;
   orienting the stabilizing device such that the bone cutting surface are perpendicular to the endplates of said vertebral bodies and the support member is parallel to said endplates;
   inserting the stabilizing device into and across the endplates such that at least a portion of at least one of the endplates is lodged between the bone cutting surface;
   rotating the stabilizing device such that at least one of the endplates is translocated perpendicular to its original location; and harvesting bone cut by said bone cutting surface.

37. A method of promoting bony fusion between a first bone and a second bone, comprising:
   providing one or more implants having a body with a longitudinal axis, and at least a first shearing means and a second shearing means offset in opposite transverse directions from the longitudinal axis;
   introducing said one or more implants in between the first and second bones;
   rotating said one or more implants about its longitudinal axis so that the first and second shearing means shear one or more fragments from the first and second bones;
   harvesting bone cut by said bone cutting surface; and
   leaving said one or more implants in position between the first and second bones.

* * * * *